US012622755B2

(12) United States Patent
Gomes Da Fonseca et al.

(10) Patent No.: US 12,622,755 B2
(45) Date of Patent: May 12, 2026

(54) METHOD AND DEVICE FOR GENERATING AN UNCERTAINTY MAP FOR GUIDED PERCUTANEOUS PROCEDURES

(71) Applicants: UNIVERSIDADE DO MINHO, Braga (PT); INSTITUTO POLITÉCNICO DO CÁVADO E DO AVE, Barcelos (PT); KARL STORZ SE & Co. KG, Tuttlingen (DE)

(72) Inventors: João Luís Gomes Da Fonseca, Santo Tirso (PT); João Luís Araújo Martins Vilaça, Braga (PT); Sandro Filipe Monteiro Queirós, Braga (PT); Estevão Augusto Rodrigues De Lima, Oporto (PT); Jorge Manuel Nunes Correia Pinto, Oporto (PT)

(73) Assignees: UNIVERSIDADE DO MINHO, Braga (PT); INSTITUTO POLITÉCNICO DO CÁVADO E DO AVE, Barcelos (PT); KARL STORZ SE & CO. KG, Tuttlingen (DE)

( * ) Notice: Subject to any disclaimer, the term of this patent is extended or adjusted under 35 U.S.C. 154(b) by 187 days.

(21) Appl. No.: 18/288,777

(22) PCT Filed: Apr. 29, 2022

(86) PCT No.: PCT/IB2022/053989
§ 371 (c)(1),
(2) Date: Oct. 27, 2023

(87) PCT Pub. No.: WO2022/229916
PCT Pub. Date: Nov. 3, 2022

(65) Prior Publication Data
US 2024/0216073 A1      Jul. 4, 2024

(30) Foreign Application Priority Data

Apr. 29, 2021 (PT) .......................................... 117202
Apr. 30, 2021 (PT) .......................................... 117204
Apr. 30, 2021 (PT) .......................................... 117205

(51) Int. Cl.
A61B 34/20        (2016.01)
A61B 34/00        (2016.01)

(52) U.S. Cl.
CPC .............. *A61B 34/20* (2016.02); *A61B 34/25* (2016.02); *A61B 2034/2051* (2016.02);
(Continued)

(58) Field of Classification Search
CPC . A61B 34/20; A61B 34/25; A61B 2034/2051; A61B 2034/2063; A61B 2034/2065
See application file for complete search history.

(56) References Cited

U.S. PATENT DOCUMENTS 7,649,981 B2      1/2010   Seppi et al.
2014/0300720 A1   10/2014  Rothberg
(Continued)

FOREIGN PATENT DOCUMENTS

EP      2590551 B1     11/2019
EP      2642917 B1     12/2019
(Continued)

OTHER PUBLICATIONS

Kellermeier et al., J Appl Clin Med Phys 2017: 18: 211-222. DOI: 10.1002/acm2.12021. (Year: 2017).*
(Continued)

*Primary Examiner* — Chao Sheng
(74) *Attorney, Agent, or Firm* — Jason H. Vick; Amped IP LLC

(57)      ABSTRACT
Guided percutaneous uncertainty mapping device and method for providing visual representations of an uncer-
(Continued)

tainty map with respect to an organ during a guided percutaneous procedure using an electromagnetic tracking (EMT) system comprising an EMT field generator and tracker, a catheter with a EMT sensor for placing in the organ to mark a percutaneous procedure target, and a needle with an EMT sensor and an electronic data processor configured for carrying out the steps of: receiving an indication of a percutaneous procedure target; receiving three-dimensional (3D) positions and orientations of the catheter and the needle tracked in real-time from the EMT system; estimating the uncertainty of the received position and orientation of the needle; estimating the uncertainty of the received position and orientation of the catheter: estimating a trajectory uncertainty of the needle departing from a current position and orientation of the needle; generating a visual representation of the estimated trajectory uncertainty and catheter uncertainty with respect to the EMT coordinate system for displaying on a user interface.

23 Claims, 7 Drawing Sheets

(52) U.S. Cl.
CPC ................. *A61B 2034/2063* (2016.02); *A61B 2034/2065* (2016.02); *A61B 2034/2068* (2016.02)

(56) References Cited

U.S. PATENT DOCUMENTS

| | | |
|---|---|---|
| 2019/0336101 A1 | 11/2019 | Chiang et al. |
| 2021/0007774 A1 | 1/2021 | Rodrigues et al. |
| 2021/0298590 A1* | 9/2021 | Ayvali .................... A61B 34/20 |

FOREIGN PATENT DOCUMENTS

| | | |
|---|---|---|
| WO | WO 2010/067188 A1 | 6/2010 |
| WO | WO 2018/222751 A1 | 12/2018 |
| WO | WO 2020/234070 A1 | 11/2020 |

OTHER PUBLICATIONS

U.S. Appl. No. 18/288,783, filed Oct. 27, 2023, Gomes Da Fonseca et al.

Eade, Ethan "Lie Groups for Computer Vision" Cambridge Univ., Cam-bridge, UK, Tech. Rep 2 (2014).
Formella, Arno et al. "Ray Tracing: A quantitative analysis and a New Practical Algorithm" The Visual Computer; vol. 11, No. 9, pp. 465-476, May 1995.
Gomes-Fonseca, Joao et al. "Surface-Based Registration Between CT and US for Image- Guided Percutaneous Renal Access—A feasibility Study" Medical Physics, vol. 46, No. 3, pp. 1115-1126, Mar. 2019.
Guan, Shao-Ya et al. "A Review of Point Feature Based Medical Image Registration" Chinese Journal of Mechanical Engineering, vol. 31, No. 1, p. 76, Dec. 2018.
Mangelson, J.G. et al. "Characterizing the Uncertainty of Jointly Distributed Poses in the Lie Algebra," arXiv. arXiv, Jun. 18, 2019.
Myronenko, Andriy et al. "Point Set Registration: Coherent Point Drift" IEEE Transactions on Pattern Analysis and Machine Intelligence, vol. 32, No. 12, pp. 2262-2275, Dec. 2010.
Oliveira, Bruno et al. "A Novel Multi-Allas Strategy with Dense Deformation Field Reconstruction for Abdominal and Thoracic Multi-Organ Segmentation from Computed Tomography" Medical Image Analysis; vol. 45, pp. 108-120, Apr. 2018.
Queiros, Sandro et al. "MITT: Medical Image Tracking Toolbox" IEEE Transactions on Medical Imaging, vol. 37, No. 11, pp. 2547-2557, Nov. 2018.
Rodrigues, Pedro L. et al. "Validation of percutaneous puncture trajectory during renal access using 4D ultrasound reconstruction" Progress in Biomedical Optics and Imaging—Proceedings of SPIE. 9415. 10.1117/12.2082528; Mar. 18, 2015.
Zhu, Hao et al. "A Review of Point Set Registration: From Pairwise Registration to Groupwise Registration" Sensors, vol. 19, No. 5, p. 1191, Mar. 2019.
International Search Report for corresponding International Application No. PCT/IB2022/053989, mailed Sep. 2, 2022.
Written Opinion for corresponding International Application No. PCT/IB2022/053989, mailed Sep. 2, 2022.
International Search Report for International Application No. PCT/IB2022/054040, mailed Sep. 2, 2022.
Written Opinion for International Application No. PCT/IB2022/054040, mailed Sep. 2, 2022.
Barfoot, Timothy D. et al. "Associating Uncertainty with Three-Dimensional Poses for Use in Estimation Problems," IEEE Trans. Robot., vol. 30, No. 3, pp. 679-693, Jun. 2014.
International Preliminary Report on Patentability for corresponding International Application No. PCT/IB2022/053989, mailed Nov. 9, 2023.
International Preliminary Report on Patentability for International Application No. PCT/IB2022/054040, mailed Nov. 9, 2023.
Notice of Allowance for U.S. Appl. No. 18/288,783, mailed Jun. 6, 2025.

* cited by examiner

WORKFLOW

| | | | |
|---|---|---|---|
| ⊗ EMT sensor | {C} Catheter | {P} Probe | {CT} Computer tomography images |
| {Tr} EMT tracker | {N} Needle | {Ta} Table | {US} Ultrasound images |

A                  B

METHOD AND DEVICE FOR GENERATING AN UNCERTAINTY MAP FOR GUIDED PERCUTANEOUS PROCEDURES

CROSS REFERENCE TO RELATED APPLICATIONS

This application is a National Phase Application under 35 U.S.C. 371 of PCT Application No. PCT/IB2022/053989 having an international filing date of 29 Apr. 2022 which designated the United States, which PCT application claimed the benefit of Portuguese Patent Application No. 117202 filed 29 Apr. 2021; Portuguese Patent Application No. 117204 filed 30 Apr. 2021; and Portuguese Patent Application No. 117205 filed 30 Apr. 2021, each of which are incorporated herein by reference in their entirety.

TECHNICAL FIELD

The present disclosure relates to a method and device for generating an uncertainty map system for providing visual representations of uncertainty during guided percutaneous procedures to an internal organ, in particular the kidney.

BACKGROUND

In percutaneous procedures, reaching a target site precisely without damaging adjacent organs or tissues is a well desired outcome. Providing tools for aiding surgeons in safely performing percutaneous procedure access is an important need addressed by the present disclosure. In particular, safely performing percutaneous procedure access to the kidney is of interest.

Document WO2018/222751 A1 discloses systems and methods for guiding the delivery of therapeutic radiation using incomplete or partial images acquired during a treatment session. A partial image does not have enough information to determine the location of a target region due to, for example, poor or low contrast and/or low SNR. The radiation fluence calculation methods described herein do not require knowledge or calculation of the target location, and yet may help to provide real-time image guided radiation therapy using arbitrarily low SNR images.

Document WO2010/067188A1 discloses a method of determining a treatment parameter, includes determining an accumulated dose at a target region that undergoes motion, determining an accumulated dose at a critical region, and determining the treatment parameter based on the determined accumulated dose at the target region and the determined accumulated dose at the critical region, wherein the act of determining the treatment parameter is performed during a treatment session. A method of determining a treatment parameter, includes tracking a position of a target, delivering radiation to the target based on the tracked position, and compensating for an inaccuracy of the tracked position by using information regarding a delivered dose to determine a treatment parameter for a next beam delivery.

These facts are disclosed in order to illustrate the technical problem addressed by the present disclosure.

General Description

The present disclosure relates to a method and device for generating an uncertainty map system for providing visual representations of uncertainty during guided percutaneous procedures to an internal organ.

The disclosure uses intraoperative images (normally US—ultrasound) tracked with an unobstructed real-time tracking system, and visual reconstructions of the intraoperative imaging data and preoperative imaging data (for example, obtained by CT—computed tomography, or by MRI—magnetic resonance imaging) of the patient's anatomy to identify targets and important anatomical structures in an internal organ, the kidney in particular, and nearby organs.

With the final purpose of reaching the target site precisely without damaging adjacent organs/tissues, a method for surgical navigation is proposed here which creates an uncertainty map to help surgeons safely perform percutaneous access. This method is used for surgical navigation during percutaneous access that computes and displays on a user interface a virtual uncertainty information based on medical imaging and tracking systems. This method estimates the uncertainty associated to the path of a tracked surgical needle, which is linked to the probability of hitting adjacent anatomical structures while trying to reach a target site defined as a physical reference inside the body. The representation of uncertainty may be obtained by changing the boundaries of the three-dimensional (3D) virtual models. Interaction, or not, between the needle boundaries and the boundaries of organs other than the target one, defines an unsafe or safe trajectory to reach the target.

One of the main advantages of the present disclosure is that it allows minimizing the risk of puncturing organs other than the organ of interest, e.g., the kidney, reducing surgical complications associated with this surgical step.

Another advantage of the disclosure is to promote a fast and straight puncturing to the organ of interest (e.g. the kidney), reducing puncture time, avoiding the formation of tortuous puncture tracts, decreasing patient harm, and improving the clinical outcome of subsequent surgical steps.

Furthermore, by providing an uncertainty assessment, when combining use of an electromagnetic real-time tracking system with reconstructions of the intraoperative data and preoperative data of the patient's anatomy, the person carrying out the procedure can use both sources of information with confidence and reliance.

Also, by providing an uncertainty assessment, the person carrying out the procedure is informed of all possible outcomes in terms of needle progression, being able to estimate clinical consequences of the possible needle destinations taking due account of said uncertainty.

In particular, the person carrying out the procedure can estimate the risk of a certain trajectory hitting undesired organs or body parts, to better plan the puncturing entry point and path, thus reducing the risk of backtracking the needle to attempt a new puncturing direction.

The provided visual representation of said uncertainty assessment enables the surgeon, i.e. the person carrying out the procedure, with a practical and perceptible way to understand the clinical situation of the needle and the patient. In particular, a visual representation based on a cylinder provides an uncluttered representation showing not only an understandable position and orientation of the needle in respect of the catheter and organ models, but also a target sight for the needle.

It is disclosed a guided percutaneous uncertainty mapping device for providing visual representations of an uncertainty map with respect to an organ during a guided percutaneous procedure using an electromagnetic tracking (EMT) system comprising an EMT field generator and tracker defining an EMT coordinate system, a catheter with an EMT sensor for placing in the organ to mark a percutaneous procedure target, a needle with an EMT sensor, and an electronic data processor configured for carrying out the steps of:

receiving an indication of a percutaneous procedure target;

receiving 3D positions and orientations of the catheter and the needle tracked in real-time from the EMT system;

estimating the uncertainty of the received position and orientation of the needle;

estimating the uncertainty of the received position and orientation of the catheter;

estimating a trajectory uncertainty of the needle departing from a current position and orientation of the needle;

generating a visual representation of the estimated trajectory uncertainty and catheter uncertainty with respect to the EMT coordinate system for displaying on a user interface.

In an embodiment for providing visual representations of the uncertainty map during the guided percutaneous procedure using an US probe with an EMT sensor, the electronic data processor is configured for previously carrying out the calibration steps of:

tracking a reference object using the EMT system, said object comprising a plurality of reference points with known positions in said object;

receiving, from the US probe, US imaging data from the reference object and, simultaneously, receiving from the EMT system a set of 3D positions and orientations of the US probe when imaging said reference object;

identifying said reference points in the received US imaging data;

calculating a probe calibration transform matrix and a probe calibration uncertainty by matching the identified reference points in the received US imaging data with the tracked reference points in an EMT coordinate system; and wherein the electronic data processor is configured for carrying out the steps of:

receiving a 3D position and orientation of the US probe tracked in real-time from the EMT system;

receiving intraoperative US imaging data from the US probe;

transforming the intraoperative US imaging data with the calculated probe calibration transform matrix;

estimating the uncertainty of the received position and orientation of the US probe;

estimating the uncertainty of the transformed intraoperative US imaging data by linearly combining, through error propagation, the calculated probe calibration uncertainty with the uncertainty of the received position and orientation of the US probe;

generating a visual representation of the estimated uncertainty of the transformed intraoperative US imaging data for displaying on a user interface.

In an embodiment, the electronic data processor is further configured for carrying out the steps of:

loading preoperative imaging data;

registering the loaded preoperative imaging data into the EMT system, by transforming the preoperative imaging data into an EMT coordinate system;

estimating the uncertainty of the registered preoperative imaging data;

generating a visual representation of the estimated uncertainty of the registered preoperative imaging data for displaying on the user interface.

In an embodiment, the electronic data processor is configured for carrying out the steps of:

loading the preoperative imaging data;

receiving a 3D position and orientation of the US probe tracked in real-time from the EMT system;

receiving intraoperative US imaging data from the US probe;

registering the loaded preoperative imaging data with the intraoperative US imaging data;

transforming the intraoperative US imaging data with the calculated probe calibration transform matrix;

transforming the registered preoperative imaging data to the EMT system with the calculated probe calibration transform matrix;

estimating the uncertainty of the received position and orientation of the US probe;

estimating the uncertainty of the transformed intraoperative US imaging data by linearly combining, through error propagation, the calculated probe calibration uncertainty with the uncertainty of the received position and orientation of the US probe;

estimating the uncertainty of the registered preoperative imaging data;

estimating an uncertainty of the registered preoperative imaging data in respect of the EMT system, by linearly combining, through error propagation, the estimated uncertainty of the transformed intraoperative US imaging data with the estimated uncertainty of the registered preoperative imaging data;

generating a visual representation of the estimated uncertainty of the transformed intraoperative US imaging data for displaying on a user interface;

generating a visual representation of the estimated uncertainty of the preoperative imaging data in respect of the EMT system for displaying on the user interface.

In an embodiment, the preoperative imaging data comprises 3D organ model or models previously reconstructed from preoperative MRI or CT images, and the estimating the uncertainty of the registered preoperative imaging data further comprises:

estimating the uncertainty of the preoperative imaging model or models;

estimating the uncertainty of the registering of the preoperative imaging data;

linearly combining, by error propagation, the estimated uncertainty of the preoperative imaging model or models with the estimated uncertainty of the registering of the preoperative imaging data;

In an embodiment, intraoperative imaging data comprises 3D organ model or models reconstructed from intraoperative US images, and the estimating of the uncertainty of the transformed intraoperative imaging data comprises:

estimating the uncertainty of the intraoperative imaging model or models;

linearly combining, by error propagation, the estimated uncertainty of the intraoperative imaging model or models with the calculated probe calibration uncertainty and with the uncertainty of the received position and orientation of the US probe.

In an embodiment, the electronic data processor is configured for calculating the uncertainty of imaging model or models, wherein said model or models comprise a plurality of vertices, by calculating and representing the uncertainty of the plurality of vertices, each said vertex having an independently calculated uncertainty.

In an embodiment, the electronic data processor is configured for calculating the uncertainty of imaging model or models, wherein said model or models comprise a plurality of vertices, by calculating and representing the uncertainty of the plurality of vertices, each said vertex having the same globally calculated uncertainty.

In an aspect of the disclosure, the organ is a kidney and the guided percutaneous procedure is a percutaneous renal access.

In an embodiment, the electronic data processor is further configured for repeatedly estimating said uncertainties and the generating said visual representations.

In an embodiment, the percutaneous procedure target is a catheter tip or a predetermined location in the coordinate system of the EMT system.

In an embodiment, estimating the uncertainty of position and orientation of an EMT sensor comprises receiving an uncertainty value from the EMT system, in particular the uncertainty value being an electromagnetic interference value from the EMT system.

In an embodiment, estimating the uncertainty of position and orientation of a certain EMT sensor further comprises using a pre-obtained calibration curve on the received electromagnetic interference value to obtain a respective calibrated uncertainty estimate.

In an embodiment, the 3D positions and orientations tracked in real-time via the EMT system are tracked through point EMT sensors.

In an embodiment, the point EMT sensors are placed on a tip of the catheter and on a tip of the needle.

In an embodiment, the user interface is a 2D display, a 3D display, a virtual-reality display or an augmented-reality display.

In an embodiment, the catheter is for positioning in a working channel in the organ by a flexible ureterorenoscope.

It is also disclosed, in an aspect of the disclosure, which is combinable with the above embodiments, a guided percutaneous uncertainty mapping device for providing visual representations of an uncertainty map with respect to an organ during a guided percutaneous procedure using an EMT system comprising an EMT field generator and tracker defining an EMT coordinate system, a catheter with a EMT sensor for placing in the organ to mark a percutaneous procedure target, a needle with an EMT sensor and an electronic data processor configured for carrying out the steps of:

receiving an indication of a percutaneous procedure target;

receiving a set of 3D positions and orientations of the catheter and the needle tracked in real-time from the EMT system;

estimating the uncertainty of the received position and orientation of the needle;

estimating the uncertainty of the received position and orientation of the catheter;

linearly combining the estimated needle and catheter uncertainties by error propagation;

estimating a trajectory uncertainty of the needle departing from a current position and orientation of the needle;

generating a visual representation of the estimated trajectory uncertainty with respect to the percutaneous procedure target for displaying on a user interface.

It is also disclosed a method as referred as being carried out by the electronic device in each of the above embodiments.

It is also disclosed a method for providing visual representations of an uncertainty map with respect to an organ during a guided percutaneous procedure using an EMT system comprising an EMT field generator and tracker defining an EMT coordinate system, a catheter with a EMT sensor for placing in the organ to mark a percutaneous procedure target, a needle with an EMT sensor and an electronic data processor, the method comprising the steps of:

receiving an indication of a percutaneous procedure target;

receiving 3D positions and orientations of the catheter and the needle tracked in real-time from the EMT system;

estimating the uncertainty of the received position and orientation of the needle;

estimating the uncertainty of the received position and orientation of the catheter;

estimating a trajectory uncertainty of the needle departing from a current position and orientation of the needle;

generating a visual representation of the estimated trajectory uncertainty and catheter uncertainty with respect to the EMT coordinate system for displaying on a user interface.

It is also disclosed a non-transitory computer-readable medium comprising computer program instructions for implementing a guided percutaneous uncertainty mapping device for providing visual representations of an uncertainty map with respect to an organ during a guided percutaneous procedure using an EMT system, which when executed by a processor, cause the processor to carry out the method of any of the described method embodiments.

BRIEF DESCRIPTION OF THE DRAWINGS

The following figures provide preferred embodiments for illustrating the disclosure and should not be seen as limiting the scope of disclosure.

DETAILED DESCRIPTION

The present disclosure relates to a method and device for generating an uncertainty map system for providing visual representations of uncertainty during guided percutaneous procedures to an internal organ and nearby organs, which will be addressed in more detail below.

Figures 1, 2:
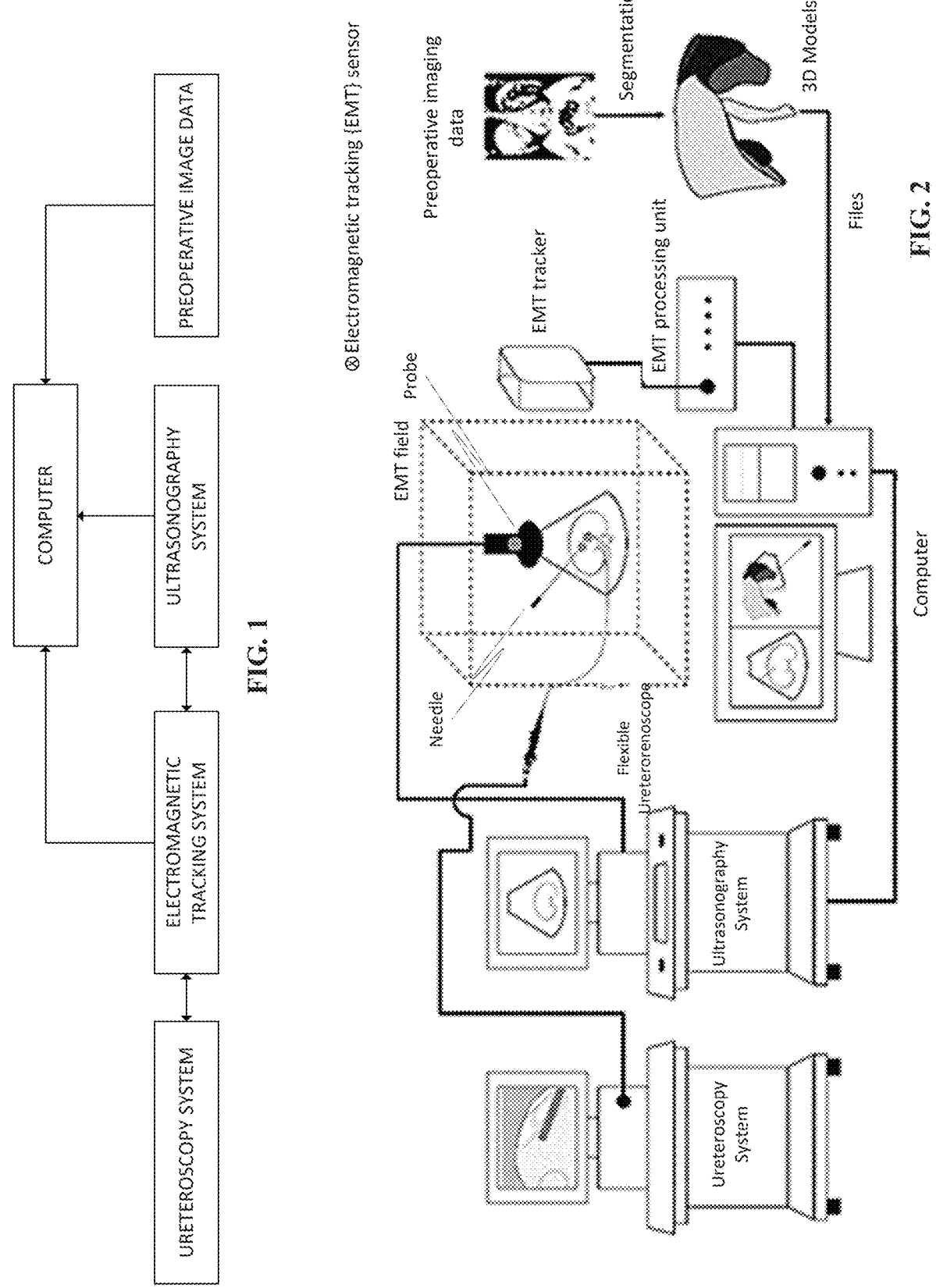
FIG. 1: Schematic conceptual representation of the systems required in an embodiment of the present disclosure.
FIG. 2: Schematic representation of an embodiment of the systems and data involved in the scope of the proposed disclosure.

FIG. 1 summarizes the systems required in this disclosure. This invention includes an electromagnetic tracking (EMT) system, a ureteroscopy system, an ultrasonography system, and a computer (i.e. electronic data processor) with navigation software where registration between pre- and intraoperative data is performed followed by computer-assisted percutaneous renal access. FIG. 2 illustrates the systems, components, and data involved in this disclosure.

In an embodiment, FIG. 1 shows an EMT system used to obtain the position and orientation of surgical instruments and reference the patient's body. The ureteroscopy system is used as a vehicle to introduce an EMT catheter into the patient's body through natural orifices, i.e. from the urethra until the renal calyx. The ultrasonography system allows the acquisition of intraoperative images of the patient being each image tracked using the EMT system. Preoperative images (e.g., computed tomography or magnetic resonance imaging) are used to enhance intraoperative data. The computer combines the whole information provided by the abovementioned systems into a virtual environment.

In an embodiment, FIG. 2 shows the proposed disclosure using an EMT system to track surgical instruments and organs, being able to reference them into the same coordinates' system (or space). A flexible ureterorenoscope is positioned inside the renal collecting system and a tracked catheter is inserted in the working channel until the tip of the flexible ureterorenoscope. A tracked probe is used to acquire US images of a patient's anatomy whose data are grabbed into the computer's memory. Preoperative imaging data are segmented, and the resulting models are used in specific navigation software, running in the computer, which registers preoperative and intraoperative imaging data to enhance percutaneous renal access. Percutaneous renal access is performed using a tracked needle which is guided until a target site (e.g., the tracked catheter or a virtual point selected by the user) in real-time.

Figure 3:
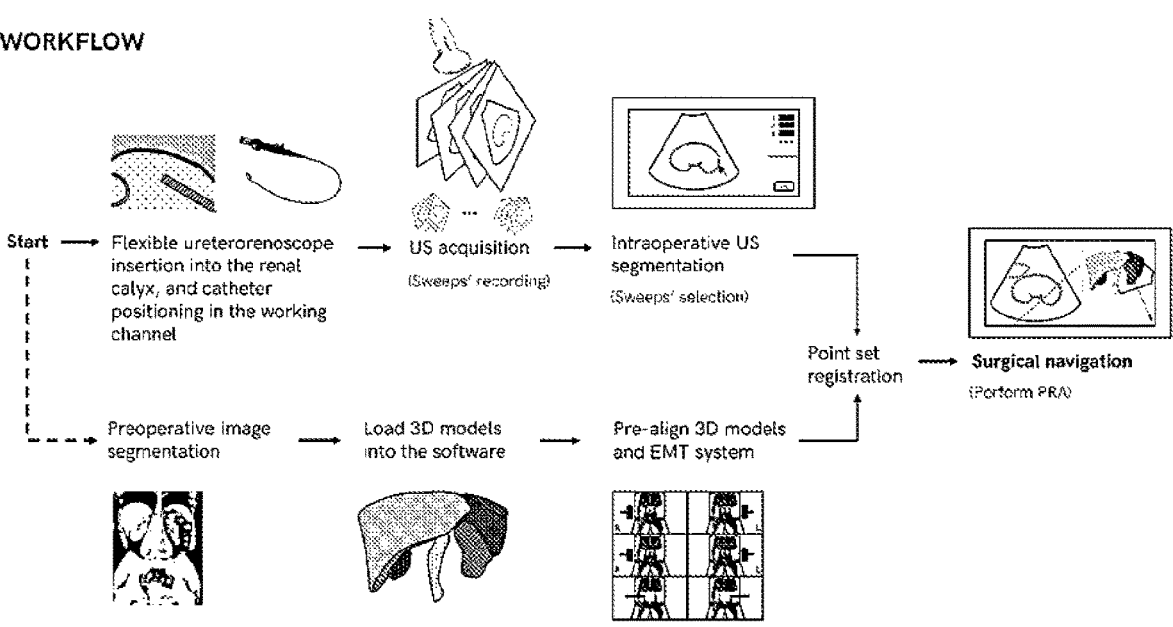
FIG. 3: Schematic representation of the clinical workflow.

In an embodiment, FIG. 3 shows, after preparing and positioning the patient for surgery, a flexible ureterorenoscope is inserted from the urethra until the renal calyx and a catheter is positioned in the working channel. The tip of catheter must be visible in the ureteroscopy imaging. Then, a US acquisition must be performed by recording several sweeps (i.e. set of US images) of the kidney and nearby organs. The selected sweeps are segmented and combined into a 3D model(s) to be registered with preoperative 3D model(s). The preoperative models are segmented and pre-align with the EMT system before the surgical procedure. Consequently, the preoperative and intraoperative data are registered using a point set registration method. Finally, both preoperative and intraoperative data are aligned and can be used to aid physician during percutaneous renal access.

The EMT system allows tracking of surgical instruments both inside and outside the patient's body. The electromagnetic sensors are rigidly attached to the US probe, needle tip, and catheter tip. Orientational and positional data of all sensors are collected by the EMT system and streamed to the computer.

Ureteroscopy is used to position the catheter in the correct calyx inside the kidney. The catheter creates a rigid relationship between the kidney and the catheter tip, allowing to track the kidney position in real-time (e.g., measuring respiratory movements) and targeting the calyx to be punctured.

Ultrasound (US) images are sent to the computer, and their position and orientation are given by the EMT sensor attached to the probe. The images and transformation data are streamed to the navigation software in real-time.

Running in a computer, the software allows the segmentation and registration of pre- and intraoperative imaging data, representing anatomical patient's data virtually. As well, this software computes and represents pose uncertainty of each element of the system. It also includes navigation features, such as the projection of the needle trajectory and catheter over the US images, as well as their visualization in the 3D virtual environment; and a needle guidance interface for visual feedback during puncture. FIG. 3 illustrates all steps required to obtain pre- and intraoperative data alignment during the surgical procedure.

The following pertains to virtual uncertainty map. This virtual uncertainty map is an estimation of the pose uncertainty of the 3D models' data in order to perform the most secure path to reach a target site. This target site can be a virtual reference by manually selecting one target point in the intraoperative imaging data using the software, or a physical reference (like a catheter with electromagnetic tracking sensor on its tip) which can be introduced by natural orifices in the human body. Using pre- and intraoperative imaging data, a virtual map of the human organs can be achieved intraoperatively. The virtual map can be obtained using specific algorithms to align imaging data, with the whole intraoperative data being referenced to the tracking system.

Figure 4:
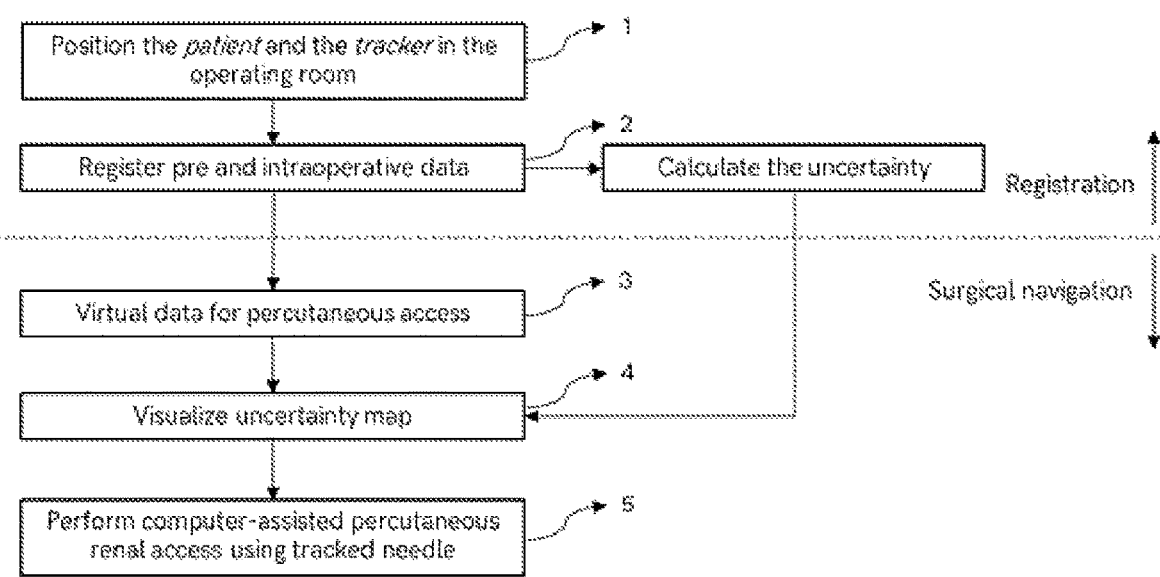
FIG. 4: Schematic representation of the flowchart of the main steps to visualize uncertainty.

In an embodiment, FIG. 4 presents a flowchart with the main steps to visualize uncertainty, from the beginning of the procedure until obtaining the uncertainty information to perform percutaneous access, where: (1) represents an optimization of the surgical position of the patient and the tracker to cover the anatomical surgical area, easing percutaneous renal access; (2) represents a pre- and intraoperative data registration performed, and uncertainties are calculated according to the selected computation mode; (3) represents a registered pre- and intraoperative data displayed in the software and used to perform renal access; (4) represents a visual representation of the calculated uncertainty on the user interface; and (5) represents performing the percutaneous renal access.

The following pertains to uncertainty computation. The pose of each component, used to virtually represent the surgical environment during percutaneous access, is represented by a transformation matrix, $T \in \mathrm{Sim}(3)$:

$$T = \begin{pmatrix} R & t \\ 0 & s^{-1} \end{pmatrix}$$

where t, R and s represent the translation vector, rotation matrix, and scale value, respectively. Pose uncertainty is represented by a covariance matrix, $C \in \mathbb{R}^{7 \times 7}$:

$$C = \begin{bmatrix} \sigma_{T_x T_x}^2 & \cdots & \sigma_{T_x s}^2 \\ \vdots & \ddots & \vdots \\ \sigma_{s T_x}^2 & \cdots & \sigma_{ss}^2 \end{bmatrix}$$

where $\sigma^2$ represents the variances and covariances between transformation elements.

The uncertainty propagation between two transformations can be computed by the compound function [1] described as:

$$(T_3, C_3) = \mathrm{compound}((T_1, C_1), (T_2, C_2))$$

where:

$$T_3 = T_1 T_2$$

$$C_3 = C_1 + Adj(T_1)C_2 Adj(T_1)^T$$

and Adj is the adjoint representation of T:

$$Adj_T = \begin{pmatrix} sR & st_\times R & -st \\ 0 & R & 0 \\ 0 & 0 & 1 \end{pmatrix}$$

with $t_x$ being the skew-symmetric matrix [2].

In view of this, each component of the system can be virtually represented by a transformation matrix, T, and since each transformation is affected by different measurements because data is tracked, acquired, segmented, and registered, a covariance matrix, C, is used to represent these uncertainties.

Figure 5:
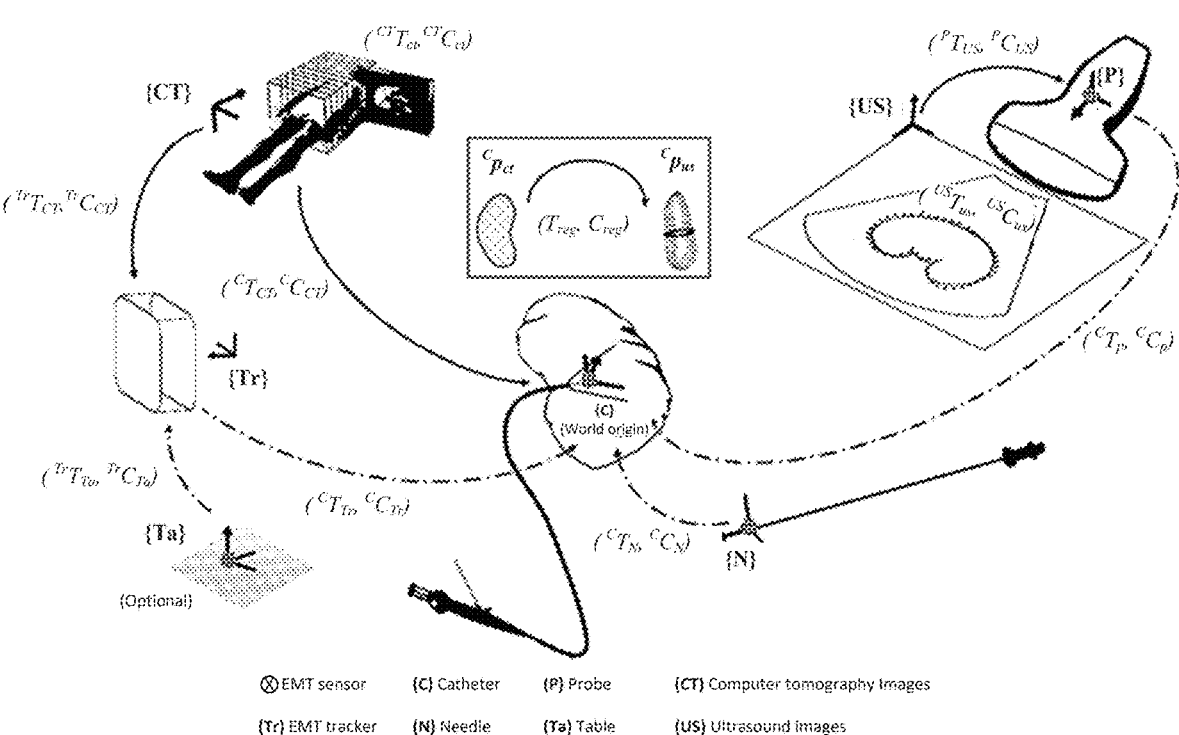
FIG. 5: Schematic representation of the overview of the components' transformations and covariances used during intraoperative use.

In an embodiment, FIG. 5 shows all transformations computed using the catheter as world origin. Dashed arrows represent transformations computed and updated from the tracked sensors in real-time, such as: tracker to catheter, $^CT_{Tr}$; probe to catheter, $^CT_P$; needle to catheter, $^CT_N$; and reference to tracker, $^{Tr}T_R$. Solid arrows represent static transformations computed pre- and intraoperatively, such as: probe calibration, $^PT_{US}$; CT to tracker prealignment, $^{Tr}T_{CT}$; CT to catheter, $^CT_{CT}=^CT_{Tr}{}^{Tr}T_{CT}$; and CT-US registration, $T_{Reg}$. Registration is performed with both models in the catheter's local coordinates (or space), i.e., $^Cp_{ct}$ and $^Cp_{us}$. $^{US}T_{us}$ and $^{CT}T_{ct}$ represent transformations between segmented models to images. Each transformation, T, can be associated with a covariance matrix, C, that describes individual sources of uncertainty. These uncertainties can be propagated along the entire system. Sensor in the surgical table can be used to inform on the real world's up-vector.

In the embodiment of this invention, the uncertainties addressed below may be considered for different components in the system.

The following pertains to catheter tip uncertainty—estimated through noise modelling of the tracking system for the EMT sensor ($^{Tr}C_c$):

$$\left(^{Tr}T_C, {}^{Tr}C_C\right)$$

The following pertains to needle tip uncertainty. This is estimated through noise modelling of the tracking system for the EMT sensor ($^{Tr}C_N$):

$$\left(^{Tr}T_N, {}^{Tr}C_N\right)$$

To reference the uncertainties from the needle tip to the catheter tip, the following operation may be computed:

$$\left(^CT_N, {}^CC_N\right) = \text{compound}\left(\left(^{Tr}T_C, {}^{Tr}C_C\right)^{-1}, \left(^{Tr}T_N, {}^{Tr}C_N\right)\right)$$

where the output of the compound function is the pose transformation, $^CT_N$, and the pose uncertainty propagation, $^CC_N$, from the needle tip to the catheter tip's coordinate system. In other words, this operation may be seen as the uncertainty composed by errors provided by the EMT sensors of the needle and catheter.

Thus, using the above function to compute transformation means:

$$^CT_N = {}^{Tr}T_C{}^{-1}{}^{Tr}T_N = {}^CT_{Tr}{}^{Tr}T_N$$

and uncertainty propagation:

$$^CC_N = inv\left(^{Tr}C_C\right) + Adj\left(^{Tr}T_C^{-1}\right)^{Tr}C_N Adj\left(^{Tr}T_C^{-1}\right)^T =$$
$$Adj\left(^{Tr}T_C^{-1}\right)^{Tr}C_C Adj\left(^{Tr}T_C^{-1}\right)^T + Adj\left(^{Tr}T_C^{-1}\right)^{Tr}C_N Adj\left(^{Tr}T_C^{-1}\right)^T$$

where inv is the inverse of the covariance, which is equal to $Adj(T^{-1})CAdj(T^{-1})^T$ [3].

Figure 6:
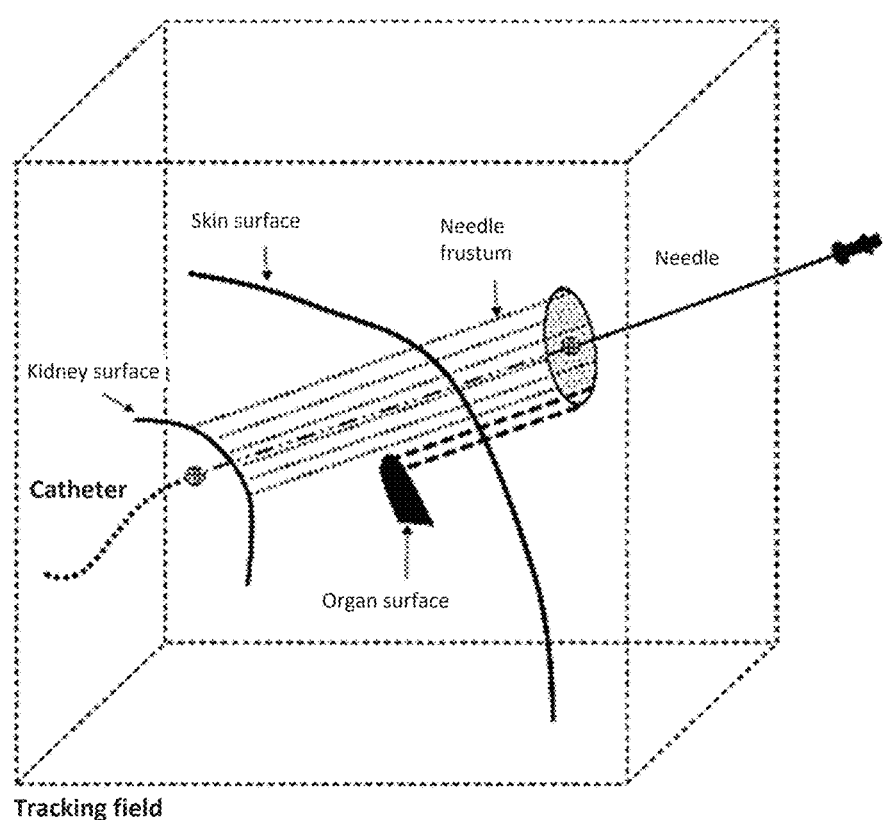
FIG. 6: Schematic representation of the cylindrical frustum representation of needle uncertainty.

In an embodiment, FIG. 6 shows a cylindrical frustum representation of needle uncertainty. If boundaries of the frustum hit any organ (represented as bold dashed lines) other than the kidney in the virtual environment, the needle trajectory is considered unsafe.

Figure 7:
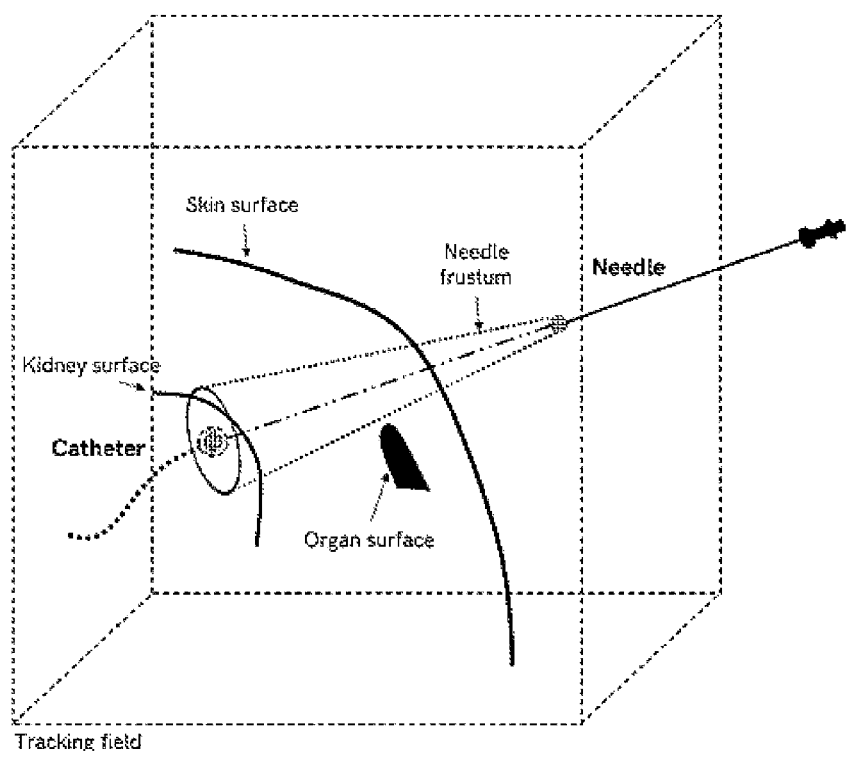
FIG. 7: Schematic representation of the conical frustum representation of needle uncertainty.

In an embodiment, FIG. 7 shows a conical frustum representation of needle uncertainty. If boundaries of the frustum hit any organ other than the kidney in the virtual environment, the needle trajectory is considered unsafe. In this representation, the needle trajectory is considered safe. Furthermore, the representation of catheter uncertainty is also represented as a sphere.

The following pertains to US organ model (e.g., kidney) uncertainty. This is estimated through noise modelling of the tracking system for the EMT sensor ($^{Tr}C_P$), noise modelling of the probe calibration ($^PC_{US}$), and noise modelling of the US segmentation ($^{US}C_{us}$):

$$\left(^{Tr}T_{us}, {}^{Tr}C_{us}\right) =$$
$$\text{compound}\left(\left(^{Tr}T_P, {}^{Tr}C_P\right), \left(\text{compound}\left(\left(^PT_{US}, {}^PC_{US}\right), \left(^{US}T_{us}, {}^{US}C_{us}\right)\right)\right)\right)$$

Here, the pose and uncertainty of the US model is propagated sequentially by this order: US model to US image (i.e. uncertainty associated to segmentation), US image to probe (i.e. uncertainty associated to probe calibration), and probe to tracker (i.e. uncertainty associated to the EMT tracker). Thus, the US model can be seen in the tracker coordinate system with an uncertainty information composed by three elements.

The following pertains to uncertainty of the CT organ model (e.g., kidney, liver, etc.). This is estimated through noise modelling of the CT segmentation ($^{CT}C_{ct}$):

$$\left(^{CT}T_{ct}, {}^{CT}C_{ct}\right)$$

The following pertains to uncertainty of the preoperative organ models after registration. This is estimated through noise modelling of CT-US registration ($C_{Reg}$, which is the same as $^{us}C_{ct}$).

$$\left(^{Tr}T_{CT}, {}^{Tr}C_{CT}\right) =$$

$$\text{compound}\left(\left(^{Tr}T_{us}, {}^{Tr}C_{us}\right), \left(\text{compound}\left(\left(^{us}T_{ct}, {}^{us}C_{ct}\right), \left(^{CT}T_{ct}, {}^{CT}C_{ct}\right)^{-1}\right)\right)\right)$$

Here, the pose and uncertainty of the registered models are propagated in this order: CT model to CT image (i.e. uncertainties associated to segmentation), CT model to US model (i.e. uncertainties associated to registration), and US model to tracker (see point 3). Thus, the preoperative models can be seen in the tracker coordinate system with an uncertainty information composed by 5 elements of the system.

Additionally, uncertainties related to registration may be refined by giving the differences between the position of the patient (specific surgical position) in the operating room (OR) and during preoperative image acquisition.

Therefore, individual parts of the surgical navigation system are modelled in the form of a covariance matrix. Some of these error models can be dynamic (i.e., obtained from the tracking system) and change during the usage of the system, while others are static (e.g., probe calibration). Static parts may be modelled individually and integrated on the system as constant matrices.

Figure 8:
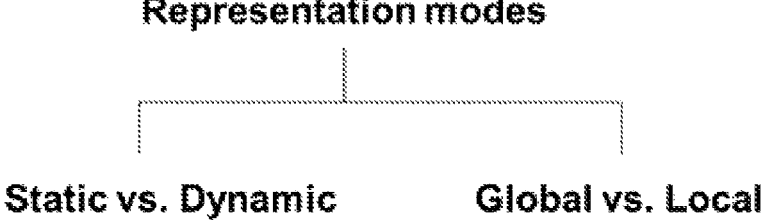
FIG. 8: Schematic representation of different representation modes for uncertainty.

The following pertains to uncertainty representation modes. The pose's uncertainty can be represented using different modes as presented in FIG. 8 and detailly explained below.

The following pertains to two possible operational embodiments of the disclosure: static mode of operation or dynamic mode of operation. Due to intrinsic measurement errors, tracking systems may influence the pose uncertainty. Static and dynamic modes may be used to represent these uncertainties by measuring them at a specific moment or during the whole process, respectively. Thus, the following matrices, which are linked to the pose information obtained from the tracking device, are considered:

$$\left(^{Tr}T_N, {}^{Tr}C_N\right)$$

$$\left(^{Tr}T_C, {}^{Tr}C_C\right)$$

$$\left(^{Tr}T_P, {}^{Tr}C_P\right)$$

The following pertains to Static. The static mode measures the pose uncertainty related to the tracking system at the moment of the registration process. The uncertainty, associated with each tracking sensor, is instantaneously saved, and kept constant during the percutaneous access. Thus, the covariance matrix and the resulting uncertainty map will not change during the whole process.

The following pertains to Dynamic. The dynamic mode measures the pose uncertainty while the system is working. The uncertainty, associated with each tracking sensor, is variable and instantaneously represented during the percutaneous access. Thus, the covariance matrix will be updated based on instantaneous estimates of the error of the sensors' transformations provided by the tracking system and related to the electromagnetic interference of equipment and/or instruments within the surgical environment.

The following pertains to two possible operational embodiments of the disclosure: local mode of operation or global mode of operation. Local and global modes may be used to compute, and hence represent, uncertainties locally or globally with respect to each 3D model, respectively.

Figure 9:
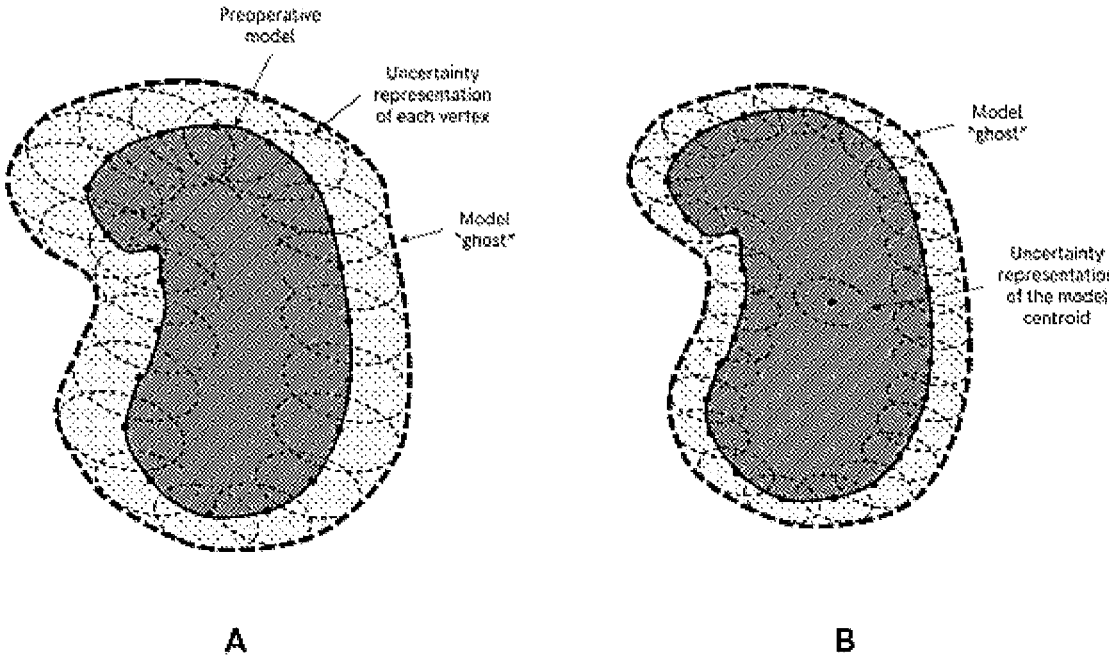
FIG. 9: Schematic representation of the computation of organ model's uncertainty.

The following pertains to Local. The local mode describes the local uncertainty of each organ. Therefore, the pose uncertainty is calculated and represented individually to each vertex of the model (FIG. 9-A). Then, using the limits of the uncertainty for each vertex, a model "ghost" encloses the pose uncertainty.

The following pertains to Global. In global mode, a simplification of the uncertainty representation is performed. Thus, a global tolerance is used. Based on the centroid of each organ model, a global uncertainty is computed and represented equally in each vertex of the model (FIG. 9-B). Similarly, using the limits of the uncertainty for each vertex, a model "ghost" encloses the pose uncertainty.

Figure 10:
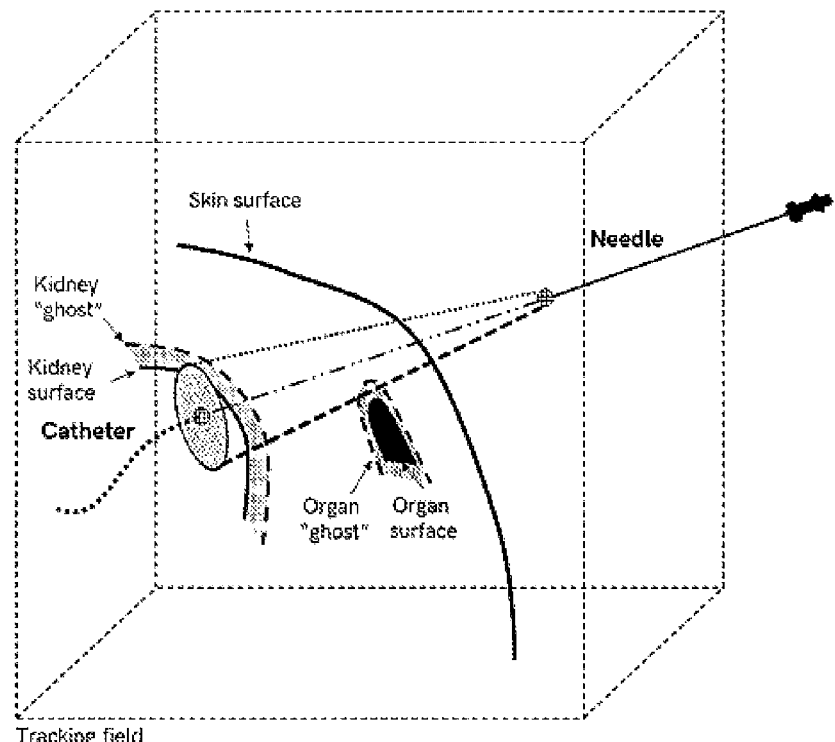
FIG. 10: Schematic representation of uncertainty applied to the organ models.

In an embodiment, FIG. 10 shows an illustration of uncertainty applied to the organ models. To reduce the probability of puncturing organs other than the kidney, "ghost" models help by representing the pose uncertainty. If the boundaries hit any organ or "ghost" other than the kidney in the virtual environment, the needle trajectory is considered unsafe (represented here as bold dashed lines).

The following pertains to possible computation modes: static-global; static-local; dynamic-global and dynamic-local.

Figure 11:
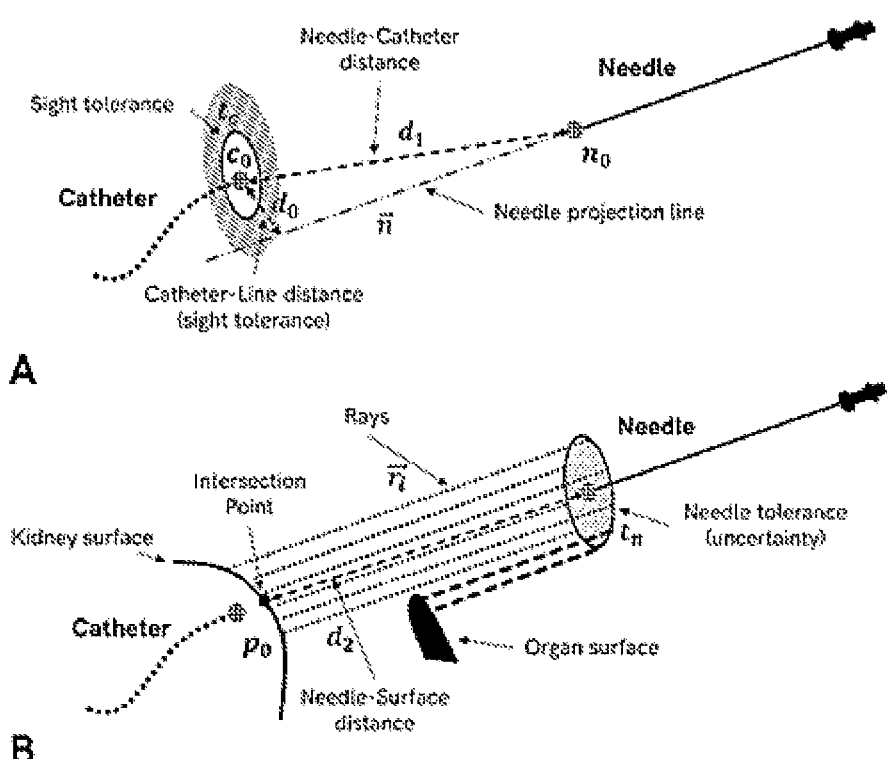
FIG. 11: Schematic representation of the principles under puncturing using uncertainty and focused on the needle.

The following pertains to models and respective uncertainties' visualization and interaction. FIG. 11 illustrates the main features used to calculate distances and possible interactions between the needle and the catheter (FIG. 11-A), and the needle and organs' models (FIG. 11-B), respectively.

In an embodiment, FIG. 11 shows an illustration of principles under puncturing using uncertainty and focused on the needle. (A) Estimation of the catheter-line distance, $d_0$, to specify if the needle trajectory is lined up with the catheter according to the sight tolerance, $t_c$. If $d_0 < t_c$, the needle trajectory is lined up. Moreover, Euclidean distance between needle and catheter, $d_1$, is also computed. (B) The needle tolerance, $t_n$, defines the path uncertainty, i.e. the cylinder diameter. Cylinder' rays, $\vec{r}_i$, are used to inspect possible interactions with organs along the needle trajectory. In this example, one organ (other than kidney, in black) is within the needle tolerance (bold and dashed lines) and the trajectory is considered unsafe. The cylinder's color represents the puncture safeness (red and green for unsafe and safe in real scenarios, respectively). The needle-surface distance, $d_2$, is also computed, i.e. the distance from the needle tip to an intersection point, $p_0$, in an organ surface.

Figure 12:
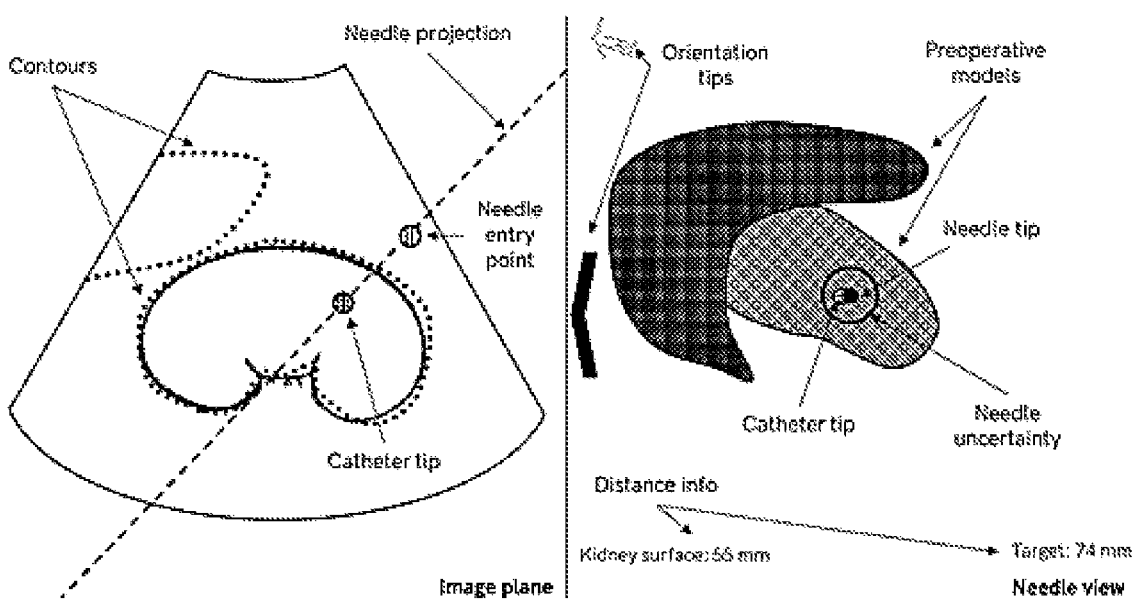
FIG. 12: Schematic representation of the graphical user interface for surgical navigation.

A specific view is proposed, also known as needle view, where a 3D visualization focused on the needle tip is seen (FIG. 12). The idea of this view is to use a sight to visually assist the puncture. The sight will help line up the needle and the catheter tip, so that the former may reach the latter easily. A sight tolerance is virtually defined around the catheter (FIG. 11-A).

In an embodiment, FIG. 12 shows the graphical user interface for surgical navigation. The environment presents two guidance views which are updated in real-time: Left: US image overlaid with needle projections and entry point, catheter tip, and contours from registered data. Right: The puncture view focused on the needle tip. Needle uncertainty is displayed. Different colors, distances information and orientation tips aid percutaneous renal access.

To measure if the needle is pointing to the catheter, the distance between the catheter and the needle projection line, $d_0$, is compute as follows:

$$d_0 = \frac{\left\| \vec{n} \times (n_0 - c_0) \right\|_2}{\left\| \vec{n} \right\|_2}$$

where x denotes the cross product, $\| \|_2$ the Euclidean norm, $\vec{n}$ the needle vector, $n_0$ the position of the EMT needle, and $c_0$ the position of the EMT catheter. If the distance, $d_0$, is lower than the defined sight tolerance, $t_c$ (e.g., 3 mm), the needle is considered accurately pointed towards the catheter.

During the procedure, guidance messages are used to alert the surgeon. If catheter and needle are lined up, the green color is used, if not, the red color. Moreover, yellow color is used to represent when the user is pointing the needle to the kidney but not correctly aligned with the catheter. Moreover, white arrows on the sides of the window indicate the required needle repositioning to point to the catheter position. This visual feedback is provided by changing the arrows' opacity value:

$$op_k = \tanh\left(\frac{d_0}{t_c}\right)|v_j|$$

where k=1, . . . , 4 represents each arrow, the tanh is the hyperbolic tangent function, and $v_j$ is a coordinate of $|\vec{v}|=[v_x, v_y]$ which is a normalized vector that defines the correction of the needle in x and y according to image plane generated based on the needle tip, $n_0$, and the needle's normal vector, $\vec{n}$.

To display the needle movements on the camera according to real needle movements during puncture (i.e., replicate up, down, right, and left movements), a transformation was applied to align the camera up-vector with the OR up-vector, which is obtained by the reference sensor ({Ta}) attached to the surgical table. Moreover, a body reference is also displayed (FIG. 12, top-left corner) which is aligned according to the intraoperative registration. This provides information about the body's pose in the OR and the camera orientation is updated according to the needle direction as well.

The Euclidean distance between the needle and catheter, $d_1=\|n_0-c_0\|_2$, is calculated and displayed on the interface (FIG. 12, bottom right corner). Moreover, the intersection point between the needle projection and organs surfaces, as well as the distance between it and the needle tip, are also computed based on ray tracing [4] (FIG. 11-B), being the intersection distance, $d_2=\|n_0-p_0\|_2$, displayed on the interface as well (FIG. 12, bottom left corner).

In FIG. 11-B, the uncertainty is embodied by the needle, which is here represented as a virtual cylinder, that defines "safe" or "unsafe" puncture paths. Thus, if the rays, $\vec{r}_i$, representing the cylinder boundaries virtually intersect a surface from an organ other than the kidney, the path is considered "unsafe", otherwise "safe".

The uncertainty information is accompanied by visual information as color code (green and yellow—safe; red—unsafe), blinking strategies, text and sound messages to provide feedback and anticipate possible interactions between organs and needle.

Thus, the needle view shows a fixed dot on the center of the GUI representing the needle tip. It displays a puncture view using the tracked needle tip as the focal point. Each needle movement redefines the displayed image, giving the perception that we are looking from the needle tip. This will give visual information if any organ is on the path, and if the needle is correctly pointing to the catheter position.

FIG. 12 is an example where the needle is pointing safely to the target (i.e. catheter) and the uncertainty is represented in the needle.

Figure 13:
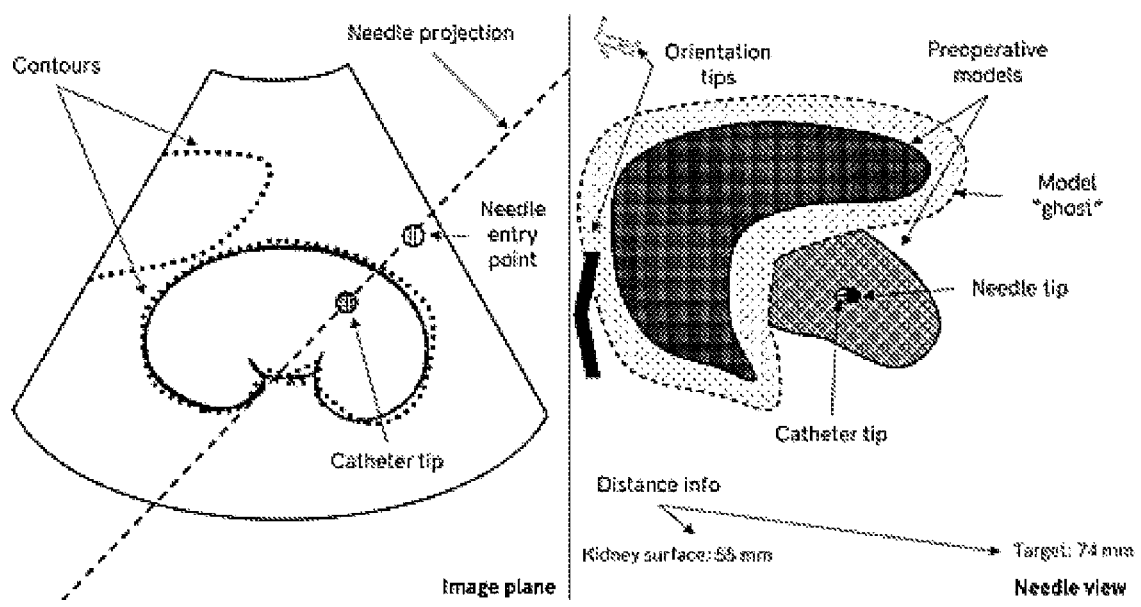
FIG. 13: Schematic representation of the graphical user interface for surgical navigation.

FIG. 13 is an example where the needle is pointing safely to the target (i.e. catheter) and the uncertainty is represented in the model (i.e. model "ghost").

Figure 14:
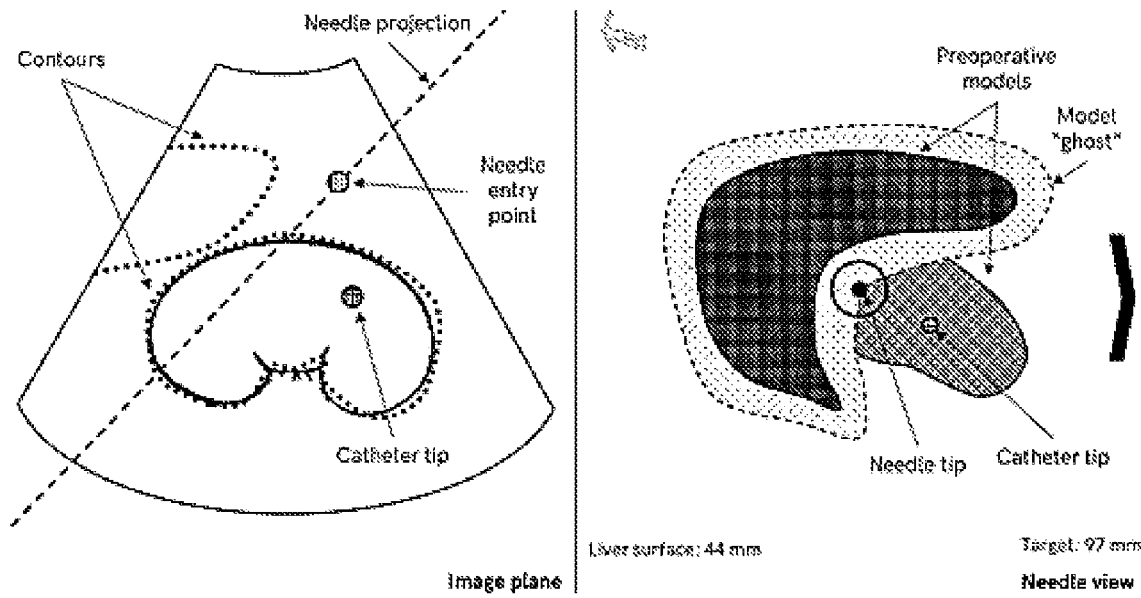
FIG. 14: Schematic representation of the graphical user interface for surgical navigation.

FIG. 14 is an example where the needle is pointing incorrectly and unsafely to the target (needle projection is pointing to the model "ghost").

In a summarized embodiment, the virtual uncertainty map is combined with a user-friendly/natural visualization interface which (FIGS. 12, 13 and 14):

Displays 3D models from pre- and intraoperative data as guidance information;

Displays a puncturing view using the tracked needle tip as the focal point (fixed center of the screen) where there is a direct relationship between screen direction and required needle movement. To display the needle movements on the monitor according to real needle movements during puncturing (i.e. movements are replicated up, down, right, left), a specific method based on the knowledge of the patient position on the OR table or using an additional tracked sensor positioned on the OR table may be essential;

Displays in real-time the trajectory and entrance point of the needle in the US image, which helps to confirm the correct path. The level of uncertainty can be inspected and level of confidence of the organs' position evaluated using tracked US images combined with needle trajectory projections;

Displays intuitive and accurate distances between target site (physical reference or virtual point) and organs' surfaces.

Alternatively, displays a puncturing view using the target site (catheter tip or a selected point) as the focal point, where it is fixed in the center of the screen and the main direction of the needle is used to partially orient the screen direction and needle tip used to select the puncturing path.

REFERENCES

[1] T. D. Barfoot and P. T. Furgale, "Associating uncertainty with three-dimensional poses for use in estimation problems," IEEE Trans. Robot., vol. 30, no. 3, pp. 679-693, 2014.

[2] E. Eade, "Lie Groups for Computer Vision."

[3] J. G. Mangelson, M. Ghaffari, R. Vasudevan, and R. M. Eustice, "Characterizing the Uncertainty of Jointly Distributed Poses in the Lie Algebra," arXiv. arXiv, 18 Jun. 2019.

[4] A. Formella and C. Gill, "Ray tracing: A quantitative analysis and a new practical algorithm," Vis. Comput., vol. 11, no. 9, pp. 465-476, September 1995.

The term "comprising" whenever used in this document is intended to indicate the presence of stated features, integers, steps, components, but not to preclude the presence or addition of one or more other features, integers, steps, components or groups thereof.

The disclosure should not be seen in any way restricted to the embodiments described and a person with ordinary skill in the art will foresee many possibilities to modifications thereof. The above described embodiments are combinable. The following claims further set out particular embodiments of the disclosure.

The invention claimed is:

1. A guided percutaneous uncertainty mapping device for providing visual representations of an uncertainty map with respect to an organ during a guided percutaneous procedure using an electromagnetic tracking (EMT) system comprising an EMT field generator and tracker defining an EMT coordinate system, a catheter with a catheter EMT sensor for placing in the organ to mark a percutaneous procedure target, a needle with a needle EMT sensor and an electronic data processor configured for carrying out the steps of:

receiving an indication of the percutaneous procedure target;

receiving three-dimensional (3D) positions and orientations of the catheter and the needle tracked in real-time from the EMT system;

estimating the uncertainty of the received position and orientation of the needle;

estimating the uncertainty of the received position and orientation of the catheter;

estimating a trajectory uncertainty of the needle departing from a current position and orientation of the needle; and generating a visual representation of the estimated trajectory uncertainty and catheter uncertainty with respect to the EMT coordinate system for displaying on a user interface.

2. The device according to claim 1, wherein the organ is a kidney and the guided percutaneous procedure is a percutaneous renal access.

3. The device according to claim 1, wherein the electronic data processor is further configured for repeatedly estimating one or more of the uncertainty of the needle, the uncertainty of the catheter and the trajectory uncertainty, and the generating said visual representations.

4. The device according to claim 1, wherein the percutaneous procedure target is a catheter tip.

5. The device according to claim 1, wherein the user interface is a 2D display, a 3D display, a virtual-reality display or an augmented-reality display.

6. The device according to claim 1, wherein the catheter is for positioning in a working channel in the organ by a flexible ureterorenoscope.

7. The device according to claim 1, for providing visual representations of the uncertainty map during the guided percutaneous procedure using an ultrasound (US) probe with a probe EMT sensor, wherein the electronic data processor is configured for previously carrying out the calibration steps of:

tracking a reference object using the EMT system, said reference object comprising a plurality of reference points with known positions in said reference object;

receiving, from the US probe, US imaging data from the reference object and, simultaneously, receiving from the EMT system a set of 3D positions and orientations of the US probe when imaging said reference object;

identifying said reference points in the received US imaging data;

calculating a probe calibration transform matrix and a probe calibration uncertainty by matching the identified reference points in the received US imaging data with the tracked reference points in the EMT coordinate system; and wherein the electronic data processor is configured for carrying out the steps of:

receiving a 3D position and orientation of the US probe tracked in real-time from the EMT system;

receiving intraoperative US imaging data from the US probe;

transforming the intraoperative US imaging data with the calculated probe calibration transform matrix;

estimating the uncertainty of the received position and orientation of the US probe;

estimating the uncertainty of the transformed intraoperative US imaging data by linearly combining, through error propagation, the calculated probe calibration uncertainty with the uncertainty of the received position and orientation of the US probe; and generating a visual representation of the estimated uncertainty of the transformed intraoperative US imaging data for displaying on the user interface.

8. The device according to claim 7, wherein the electronic data processor is configured for carrying out the steps of:

loading the preoperative imaging data;

receiving a 3D position and orientation of the US probe tracked in real-time from the EMT system;

receiving intraoperative US imaging data from the US probe;

registering the loaded preoperative imaging data with the intraoperative US imaging data;

transforming the intraoperative US imaging data with the calculated probe calibration transform matrix;

transforming the registered preoperative imaging data to the EMT system with the calculated probe calibration transform matrix;

estimating the uncertainty of the received position and orientation of the US probe;

estimating the uncertainty of the transformed intraoperative US imaging data by linearly combining, through error propagation, the calculated probe calibration uncertainty with the uncertainty of the received position and orientation of the US probe;

estimating the uncertainty of the registered preoperative imaging data;

estimating an uncertainty of the registered preoperative imaging data in respect of the EMT system, by linearly combining, through error propagation, the estimated uncertainty of the transformed intraoperative US imaging data with the estimated uncertainty of the registered preoperative imaging data;

generating a visual representation of the estimated uncertainty of the transformed intraoperative US imaging data for displaying on a user interface; and generating a visual representation of the estimated uncertainty of the preoperative imaging data in respect of the EMT system for displaying on the user interface.

9. The device according to claim 7, wherein intraoperative imaging data comprises 3D organ model or models reconstructed from intraoperative US images, and the estimating of the uncertainty of the transformed intraoperative imaging data comprises:

estimating the uncertainty of the intraoperative imaging model or models; and linearly combining, by error propagation, the estimated uncertainty of the intraoperative imaging model or models with the calculated probe calibration uncertainty and with the uncertainty of the received position and orientation of the US probe.

10. The device according to claim 2, wherein estimating the uncertainty of position and orientation of at least one of the catheter, needle, and probe comprises receiving an uncertainty value from the EMT system, the uncertainty value being an electromagnetic interference value from the EMT system.

11. The device according to claim 10, wherein estimating the uncertainty of position and orientation of a certain of the catheter, needle or probe further comprises using a pre-obtained calibration curve on the received electromagnetic interference value to obtain a respective calibrated uncertainty estimate.

12. The device according to claim 1, wherein the electronic data processor is further configured for carrying out the steps of:

loading preoperative imaging data;

registering the loaded preoperative imaging data into the EMT system;

estimating the uncertainty of the registered preoperative imaging data; and generating a visual representation of the estimated uncertainty of the registered preoperative imaging data for displaying on the user interface.

13. The device according to claim 12, wherein the preoperative imaging data comprises 3D organ model or models previously reconstructed from preoperative MRI or CT images, and the estimating the uncertainty of the registered preoperative imaging data further comprises:

estimating the uncertainty of the preoperative imaging model or models;

estimating the uncertainty of the registering of the preoperative imaging data; and linearly combining, by error propagation, the estimated uncertainty of the preoperative imaging model or models with the estimated uncertainty of the registering of the preoperative imaging data.

14. The device according to claim 13, wherein the electronic data processor is configured for calculating the uncertainty of the preoperative imaging model or models, wherein said preoperative imaging model or models comprise a plurality of vertices, by calculating and representing the uncertainty of the plurality of vertices, each said vertex having an independently calculated uncertainty.

15. The device according to claim 13, wherein the electronic data processor is configured for calculating the uncertainty of the preoperative imaging model or models, wherein said preoperative imaging model or models comprise a plurality of vertices, by calculating and representing the uncertainty of the plurality of vertices, each said vertex having the same globally calculated uncertainty.

16. The device according to claim 1, wherein the 3D positions and orientations tracked in real-time via the EMT system are tracked through point EMT sensors.

17. The device according to claim 16, wherein the point EMT sensors are placed on a tip of the catheter and on a tip of the needle.

18. A guided percutaneous uncertainty mapping device for providing visual representations of an uncertainty map with respect to an organ during a guided percutaneous procedure using an electromagnetic tracking (EMT) system comprising an EMT field generator and tracker defining an EMT coordinate system, a catheter with a catheter EMT sensor for placing in the organ to mark a percutaneous procedure target, a needle with a needle EMT sensor and an electronic data processor configured for carrying out the steps of:

receiving an indication of the percutaneous procedure target;

receiving a set of 3D positions and orientations of the catheter and the needle tracked in real-time from the EMT system;

estimating the uncertainty of the received position and orientation of the needle;

estimating the uncertainty of the received position and orientation of the catheter;

linearly combining the estimated needle and catheter uncertainties by error propagation;

estimating a trajectory uncertainty of the needle departing from a current position and orientation of the needle; and generating a visual representation of the estimated trajectory uncertainty with respect to the percutaneous procedure target for displaying on a user interface.

19. A method for providing visual representations of an uncertainty map with respect to an organ during a guided percutaneous procedure using an electromagnetic tracking (EMT) system comprising an EMT field generator and tracker defining an EMT coordinate system, a catheter with a catheter EMT sensor for placing in the organ to mark a percutaneous procedure target, a needle with a needle EMT sensor and an electronic data processor, the method comprising:

receiving an indication of the percutaneous procedure target;

receiving 3D positions and orientations of the catheter and the needle tracked in real-time from the EMT system;

estimating the uncertainty of the received position and orientation of the needle;

estimating the uncertainty of the received position and orientation of the catheter;

estimating a trajectory uncertainty of the needle departing from a current position and orientation of the needle; and generating a visual representation of the estimated trajectory uncertainty and catheter uncertainty with respect to the EMT coordinate system for displaying on a user interface.

20. The method according to claim 19, wherein the method further comprises:

loading the preoperative imaging data;

receiving a 3D position and orientation of the US probe tracked in real-time from the EMT system;

receiving intraoperative US imaging data from the US probe;

transforming the intraoperative US imaging data with the calculated probe calibration transform matrix;

registering the loading preoperative imaging data with the transformed intraoperative US imaging data;

estimating the uncertainty of the received position and orientation of the US probe;

estimating the uncertainty of the transformed intraoperative US imaging data by linearly combining, through error propagation, the calculated probe calibration uncertainty with the uncertainty of the received position and orientation of the US probe;

estimating the uncertainty of the registered preoperative imaging data;

estimating an uncertainty of the registered preoperative imaging data in respect of the EMT system, by linearly combining, through error propagation, the estimated uncertainty of the transformed intraoperative US imaging data with the estimated uncertainty of the registered preoperative imaging data;

generating a visual representation of the estimated uncertainty of the transformed intraoperative US imaging data for displaying on a user interface; and generating a visual representation of the estimated uncertainty of the preoperative imaging data in respect of the EMT system for displaying on the user interface.

21. The method according to claim 19, for providing visual representations of the uncertainty map during the guided percutaneous procedure using an US probe with an EMT sensor, wherein the method comprises previously carrying out the calibration including:

tracking a reference object using the EMT system, said reference object comprising a plurality of reference points with known positions in said reference object;

receiving, from the US probe, US imaging data from the reference object and, simultaneously, receiving from the EMT system a set of 3D positions and orientations of the US probe when imaging said reference object;

identifying said reference points in the received US imaging data;

calculating a probe calibration transform matrix and a probe calibration uncertainty by matching the identified reference points in the received US imaging data with the tracked reference points in the EMT coordinate system; and wherein the method comprises:

receiving a 3D position and orientation of the US probe tracked in real-time from EMT system;

receiving intraoperative US imaging data from the US probe;

transforming the intraoperative US imaging data with the calculated probe calibration transform matrix;

estimating the uncertainty of the received position and orientation of the US probe;

estimating the uncertainty of the transformed intraoperative US imaging data by linearly combining, through error propagation, the calculated probe calibration uncertainty with the uncertainty of the received position and orientation of the US probe; and generating a visual representation of the estimated uncertainty of the transformed intraoperative US imaging data for displaying on the user interface.

22. The method according to claim 19 wherein the method further comprises:

loading preoperative imaging data;

registering the loaded preoperative imaging data into the EMT system;

estimating the uncertainty of the registered preoperative imaging data; and generating a visual representation of the estimated uncertainty of the preoperative imaging data for displaying on the user interface.

23. A non-transitory computer-readable information storage medium comprising computer program instructions for implementing a guided percutaneous uncertainty mapping device for providing visual representations of an uncertainty map with respect to an organ during a guided percutaneous procedure using an EMT system, which when executed by a processor, cause the processor to carry out the method of comprising:

receiving an indication of a percutaneous procedure target:

receiving 3D positions and orientations of the catheter and the needle tracked in real-time from the EMT system;

estimating the uncertainty of the received position and orientation of the needle;

estimating the uncertainty of the received position and orientation of the catheter;

estimating a trajectory uncertainty of the needle departing from a current position and orientation of the needle; and generating a visual representation of the estimated trajectory uncertainty and catheter uncertainty with respect to the EMT coordinate system for displaying on a user interface.

*     *     *     *     *